United States Patent
Fencl et al.

[11] Patent Number: 5,866,076
[45] Date of Patent: Feb. 2, 1999

[54] SINGLE ENDED GERMICIDAL LAMP FOR HVAC SYSTEMS

[75] Inventors: Forrest B. Fencl, Huntington Beach; Robert M. Culbert, Manhattan Beach, both of Calif.

[73] Assignee: Steril-Aire U.S.A., Inc., Cerritos, Calif.

[21] Appl. No.: 773,643

[22] Filed: Dec. 24, 1996

[51] Int. Cl.⁶ ............................. A61L 9/20; H01R 33/945
[52] U.S. Cl. ..................... 422/121; 350/454.11; 362/226
[58] Field of Search .......... 422/24, 121; 313/25, 313/318.01, 318.05, 318.07, 318.1, 318.09, 623, 624, 625, 49–51, 269, 163; 174/52.1, 52.2, 52.3, 53.58, 59.61, 65 R, 65 G; 220/3.2, 2.1 R; 248/230.7, 231.81, 291.1, 294.1; 439/602, 611; 24/489, 517, 518, 546, 547, 555, 556

[56] References Cited

U.S. PATENT DOCUMENTS

| | | |
|---|---|---|
| 2,365,342 | 12/1944 | Hilliard et al. . |
| 2,586,940 | 2/1952 | Graham . |
| 2,778,588 | 1/1957 | Capocci . |
| 4,179,616 | 12/1979 | Coviello et al. ..................... 250/527 |
| 4,390,432 | 6/1983 | Takeguchi et al .................. 422/24 X |
| 4,971,687 | 11/1990 | Anderson ............................ 422/24 X |
| 4,990,313 | 2/1991 | Pacosz .................................. 422/121 |
| 5,266,215 | 11/1993 | Engelhard ........................... 422/24 X |
| 5,334,905 | 8/1994 | Ullrich ................................ 422/24 X |
| 5,505,904 | 4/1996 | Haidinger et al. ............... 422/121 X |
| 5,701,050 | 12/1997 | Wolf et al. ........................ 422/24 X |

FOREIGN PATENT DOCUMENTS

95/17634  6/1995  WIPO .

OTHER PUBLICATIONS

Light Sources, Inc., Germipak UV Cells spec sheet (admitted prior art).
Light Sources, Inc., Your Own Style Lamp Base brochure (admitted prior art).
Modern Medical Systems, Products and Systems for Protection from Airborne Tuberculosis Bacillus brochure (admitted prior art).

*Primary Examiner*—E. Leigh McKane
*Attorney, Agent, or Firm*—Steven Sereboff; Sereboff & Buyan, LLP

[57] ABSTRACT

A germicidal lamp is disclosed. The lamp's tube has a single stem and may be installed in the lamp's fixture without touching the tube's envelope. The fixture includes a mounting mechanism and a damping mechanism which ease installation and render the tube less susceptible to adverse forces.

15 Claims, 4 Drawing Sheets

SINGLE ENDED GERMICIDAL LAMP FOR HVAC SYSTEMS

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure, as it appears in the Patent and Trademark Office patent files or records, but otherwise reserves all copyright and trade dress rights whatsoever.

BACKGROUND OF THE INVENTION

1. Field of the Invention

The present invention relates generally to germicidal lamps, and more particularly the invention relates to such devices used in air and surface sterilization.

2. Description of Related Art

Germicidal lamps have been known for quite a while. Typically, a germicidal lamp has two primary parts, a tube and a base (or fixture). The tube is typically a long, thin sealed hollow cylinder containing a discrete amount of inert gas and liquid mercury. These tubes are made in standard sizes and power capabilities, and have standardized outputs. Standard tubes are made by General Electric (G25 T8 and G36 T6), Sylvania and others. These standard tubes have lengths of 18 or 36 inches.

The fixture of a germicidal lamp is designed such that the tube may be easily installed and removed, while holding the tube firmly during other times. The fixture typically also incorporates a ballast. The ballast is an electrical component that converts a standard power input (e.g., 117 V, 1 A 60 Hz AC household current) to a form appropriate to the tube. Typically germicidal lamps use the same standard magnetic ballasts as used by fluorescent lamps. These ballasts deliver electricity of 400 V, 420 mA and 60 Hz to the tube.

Germicidal lamps typically are available in standard form factors. The standard tubes described above fit into a standard base, which is 18 or 36 inches long. The ballast is disposed at one end of the fixture inside a casing, and the fixture has sockets at either end to provide mechanical support for the tube and electrical contacts. The typical fixture is a shiny metal such as aluminum or steel.

Germicidal tubes differ significantly from electric discharge devices used in ultraviolet gas spectroscopy (VUV tubes). Germicidal tubes are low pressure and emit ultraviolet light at the primary and secondary emission lines of mercury—254 nm and 187 nm. In contrast, VUV tubes are high pressure tubes, operate at very high temperatures and emit light at different spectra.

Typical germicidal lamps create ozone. Along with mercury's primary emission at 254 nm, there is a second, but frequently large amount of radiation at 187 nm. This secondary emission results in ozone creation. In the typical application of a germicidal lamps, this ozone is desirable as a germicide.

One common use of germicidal lamps is in water treatment. In water treatment, ozone is generally considered very desirable. However, the ozone in these water treatment systems is very controlled. The ultraviolet tubes are typically enclosed in quartz glass sleeves which restrict air flow, thereby elevating ambient temperatures. This is necessary because the water would otherwise draw away heat from the tube, shutting down the tube.

Although it has long been known that germicidal lamps may be used for air sterilization, their actual implementation has been fairly limited. One reason for this is the ozone creation already discussed. Ozone is harmful to humans, and is a known carcinogen.

Another reason that germicidal lamps have not been use for air sterilization has been skin-effect cooling. According to several publications, a germicidal tube operates best at temperatures well above room temperature, and include heaters to vaporize the liquid mercury.

In skin-effect cooling, air moving across the outside of a tube reduces the normal operating temperature. As the temperature drops, the mercury vapor pressure drops, leading to a drop in ultraviolet output. It is known that if the ambient temperature drops below 72° F. or air is blown over the tube, ultraviolet output of standard germicidal tubes drops at an extremely rapid rate—as much as a 75% depreciation of output at approximately 58° F. Furthermore, the tubes age quicker at low temperatures.

Because of skin-effect cooling, 2 to 4 times as many standard germicidal lamps must be used in low temperature applications to maintain output, and the tubes must be replaced more often—every 2500 hours. The high cost of extra tubes and the maintenance costs have limited the practicality of germicidal lamps.

There have been numerous attempts to use standard germicidal lamps in operating rooms and hospitals. However, higher output tubes used in these applications produce large amounts of ozone, which as mentioned, is undesirable. This limits their applicability. Furthermore, the germicidal lamps have been used in the upper reaches of rooms, thus limiting their utility.

Despite the clear benefits of germicidal lamps, problems such as ozone, depressed output in low temperatures and short tube life have prevented their use in all but highly specialized applications. One area which has long sought to use germicidal lamps is the heating, ventilation and air conditioning (HVAC) industry. HVAC systems typically comprise fans, ducts and valves for moving air where needed. An HVAC system may also include a cooling plant and a heating plant for, respectively, cooling and heating the air. In most systems, air is drawn in, filtered, cooled or heated, humidified, and then delivered to a room. Air is also drawn from the room for recirculation through the HVAC system. The HVAC industry has adapted standards for the rate of air exchange in a room, as well as standards for introduction of fresh air into an otherwise closed HVAC system.

Although numerous companies have attempted to provide germicidal lamps for HVAC, the standard germicidal lamps have been unsatisfactory. Typically, a standard germicidal lamp is installed in the HVAC system or in a room where the air is still or warm.

Typical germicidal lamps cannot operate in the harsh environments of HVAC systems. HVAC systems typically are used for controlling the temperature, humidity and comfort of the air in various spaces. Such spaces include offices, living spaces, commercial spaces, industrial spaces, and the interior of vehicles such as cars, buses, planes and ships. The HVAC systems necessarily deliver air which has a temperature, humidity and flow rate which are deleterious to germicidal lamp operation, and the frequent changes of temperature, humidity and flow rate further destabilize these standard germicidal lamps.

More recently, the HVAC industry has also focused on indoor air quality (IAQ). In addition to temperature, humidity and comfort, IAQ addresses the components of air and how the air's components may be controlled to enhance comfort, health and other needs. Often, the goal of HVAC systems is to provide especially clean air, be it for semiconductor or pharmaceutical processing facilities or hospitals and homes.

One reason that fresh air is introduced is because of the existence and growth of molds, spores, bacteria and viruses in the HVAC system. However, introducing fresh air and increasing air exchange rates requires bigger ducts, more powerful fans, more powerful heating and cooling plants, and a lot more power to operate these.

Where it is attempted to install standard germicidal lamps in an HVAC system, installation requires human access to the interior of the duct and typically requires the cutting of an access door or a large opening for the fixture. Furthermore, standard 18" or 36" germicidal lamps are either too large or too small for HVAC ducts. Use of these lamps results in either poor UV coverage of the target area, or the use of any lamps with over-coverage. With over-coverage, installation, usage and maintenance costs rise. To provide adequate ultraviolet dose with low output lamps, bulky and expensive racks have been proposed. Yet, these racks nonetheless require significant engineering and manufacturing efforts.

It is therefore the object of the invention to provide a germicidal lamp suited for use in HVAC systems. Such a germicidal lamp would be easy to install and service, and be able to operate for long periods within the HVAC system and not generate appreciable amounts of ozone. These objects and others are provided by the of the present invention.

SUMMARY OF THE INVENTION

The previously described objects are achieved in a germicidal lamp which, in accordance with a preferred embodiment of the present invention, the lamp comprises a tube and a fixture in which the tube is supported at one end only by the fixture, and the fixture is mountable on a single wall outside of a duct. Thus, the tube spans across the interior of the duct without necessitating access to the interior of the duct and provides complete coverage without over-coverage.

The germicidal lamp of the invention is sized so that the tube will span across a standard HVAC duct. Because the germicidal lamps of the invention fit in standard HVAC ducts, fewer lamps are needed and installation and maintenance are further eased.

The fixture has a socket into which the tube is inserted and a mounting mechanism for holding the fixture firmly in the fixture. An added advantage of the mounting mechanism of the invention is that it absorbs shocks to the tube.

With the single-ended germicidal lamp of the invention, installation requires little more than creating a small hole in the wall of an air duct, mounting the fixture on the outside of the duct wall, inserting the tube through the hole and locking the tube into the fixture. Alternatively, the fixture may be mounted on the inside of the duct's wall, eliminating the need for a hole in the duct's wall.

Beside easy installation, the single-ended germicidal lamp of the invention is also easily maintained. A further aspect of the invention provides an access panel in the fixture opposite where the tube emerges. Tube removal requires little more than removing the access panel, removing the socket from the tube, releasing the mounting mechanism, and pulling the tube out of the duct. A new tube may then be inserted in the opposite order. A further advantage of this access panel is easy access to the ballast.

A further aspect of the tube and fixture of the invention are their ability to deliver high levels of ultraviolet radiation at low temperatures and in fast moving air. To achieve this, the tube is biased to operate in still, warm air at a higher temperature than is optimal, and the ballast delivers higher currents to drive the tube to the higher temperature. When cool or moist air runs across the tube, the skin-effect cooling drops the tube's temperature to a more optimal temperature, thus increasing ultraviolet output. To further enhance output and improve stability, the ballast drives the tube at a higher frequency than standard.

Still further objects and advantages attaching to the device and to its use and operation will be apparent to those skilled in the art from the following particular description.

DESCRIPTION OF THE DRAWINGS

These and other advantages of the present invention are best understood with reference to the drawings, in which, in varying detail.

These and additional embodiments of the invention may now be better understood by turning to the following detailed description wherein an illustrated embodiment is described.

DETAILED DESCRIPTION OF THE INVENTION

Throughout this description, the preferred embodiment and examples shown should be considered as exemplars, rather than limitations on the apparatus and methods of the present invention.

Figures 1A, 2:
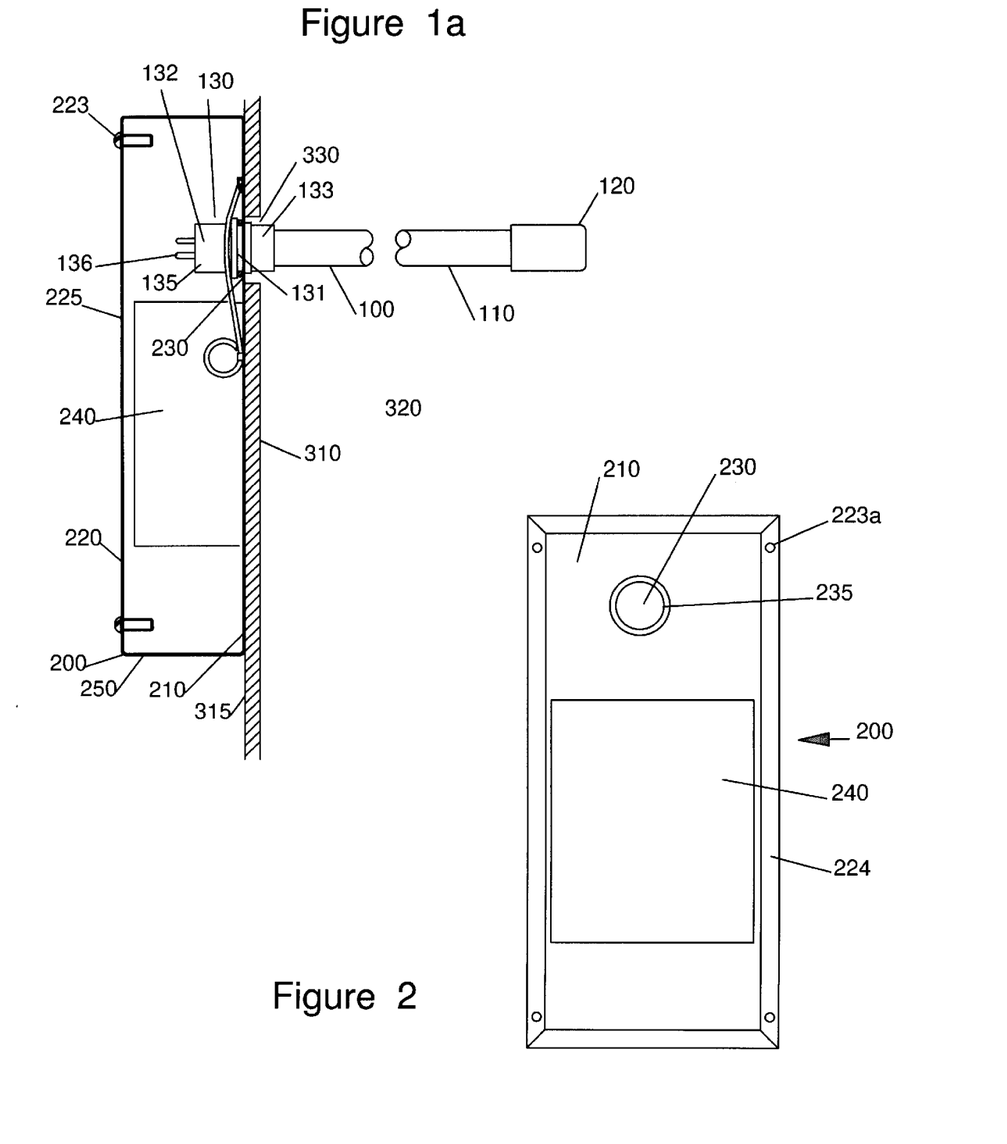
FIG. 1A is a partial side view of a germicidal lamp for external mounting.
FIG. 2 is a front view of the device of FIG. 1A.

Referring now to FIG. 1A, there is shown a single-tube, single-ended germicidal lamp in accordance with the invention for mounting outside of an air duct. The lamp is shown installed in an air duct having a wall 310 with an outer surface 315. The air duct defines an air passage 320.

The lamp comprises a tube 100 and a fixture 200. The fixture 200 is mounted to the outer surface 315 of the wall 310. The tube 100 extends from where it is mounted in the fixture 200 into the air passage 320.

The tube passes through an insertion hole 330 in the wall 310. In general, air ducts do not have holes suitable for use as described and such a hole must be created during installation of the germicidal lamp. Preferably, the insertion hole 330 is made slightly larger than the tube 100 so that the tube 100 may pass there through and also may move slightly in response to shocks or pressure. The insertion hole 330 should be small enough that the fixture 200 will entirely cover the insertion hole, thereby closing air leaks.

The fixture 200 preferably comprises a hollow box-like casing with a first wall 210 and a second wall 220. The first wall 210 has a through-hole 230. Preferably, the through-hole 230 is just large enough for the tube 100 to pass there through. The fixture further comprises side walls 250.

The second wall 220 includes an access door 225. As shown, the access door 225 extends across the second wall 220 and is attached to the body of the fixture 200 with screws 223. Alternatively, the access door 225 may be hinged to the body of the fixture 200, or attached with other means which permit the access door 225 to be moved from the body of the fixture 200 to create an opening therein through which tubes may be inserted and removed as described below.

The fixture 200 further includes a ballast 240. The ballast 240 may be of the type known in the art and is provided for converting available electrical power, typically 110 V, 60 Hz into a form for driving the tube 100. Preferably, the ballast is electronic (i.e., not magnetic) and outputs 450 V to start the tube and 40–50 V at 20 kHz during normal operation.

FIG. 2 shows the fixture 200 with the access door 225 removed. In the preferred embodiment, the second wall 220 comprises flanges 224 which are extensions of the side walls 250, cut and bent perpendicular to the side walls 250. The fixture 200 includes screw holes 223a in each corner. The access door 225 rests on the flanges 224 and is held securely to the flanges 224 by the screws 223.

As shown in FIG. 2, surrounding the through-hole 230 in the first wall 210 is a flange 235. The flange 235 is preferably round and protrudes a small distance away from the first wall 210. One purpose of the flange 235 is to provide a smooth surface against which the tube 100 may slide during insertion and removal.

Referring again to FIG. 1A, the tube 100 comprises an envelope 110 and a stem 135. The stem 135 includes a number of leads 136. The leads 136 provide electrical contacts to the tube 100.

The envelope 110 comprises a hollow quartz glass cylinder. The envelope 110 extends partially into the stem 135. The tube 100 has two ends, a leadless free end 120 and a stemmed end 130 having the stem 135. The envelope 110 is sealed at the ends 120, 130, and contains a starting gas such as argon, neon, xenon or krypton, or a mixture of such gases, and a quantity of vaporizable metal therein, preferably mercury, the vapor of which emits ultraviolet light during the operation of the device. Preferably the quantity of metal is such that it is wholly vaporized at the operating temperature of the tube 100.

In one embodiment, the tube 100 has electrodes (not shown) at each end 120, 130. Since the free end 120 is leadless, the tube includes wires spanning from the electrodes in the free end 120 to the leads 136 in the stem 135. More particularly, the wires run from the electrodes in the free end 120, out of the free end 120, along the outside of the envelope 110 and into the stem 135 to the leads 136.

The stem 135 preferably comprises a stub 132, a ring 131 and a hub 133. The ring 131, stub 132 and hub 133 preferably are formed as a unit and are of a rigid, heat resistant, insulating material such as ceramic. The stub 132, ring 131 and hub 133 are preferably cross-sectionally round. The hub 133 preferably has a diameter a small amount less than the diameter of the through-hole 230. The ring 131 has a diameter larger than that of the through-hole 230. Accordingly, the ring 131 prevents the tube 100 from slipping through the through-hole 230. The stub 132 preferably has a diameter smaller than that of the ring 131 and may be of the same diameter as the hub 133.

Figures 1B, 3:
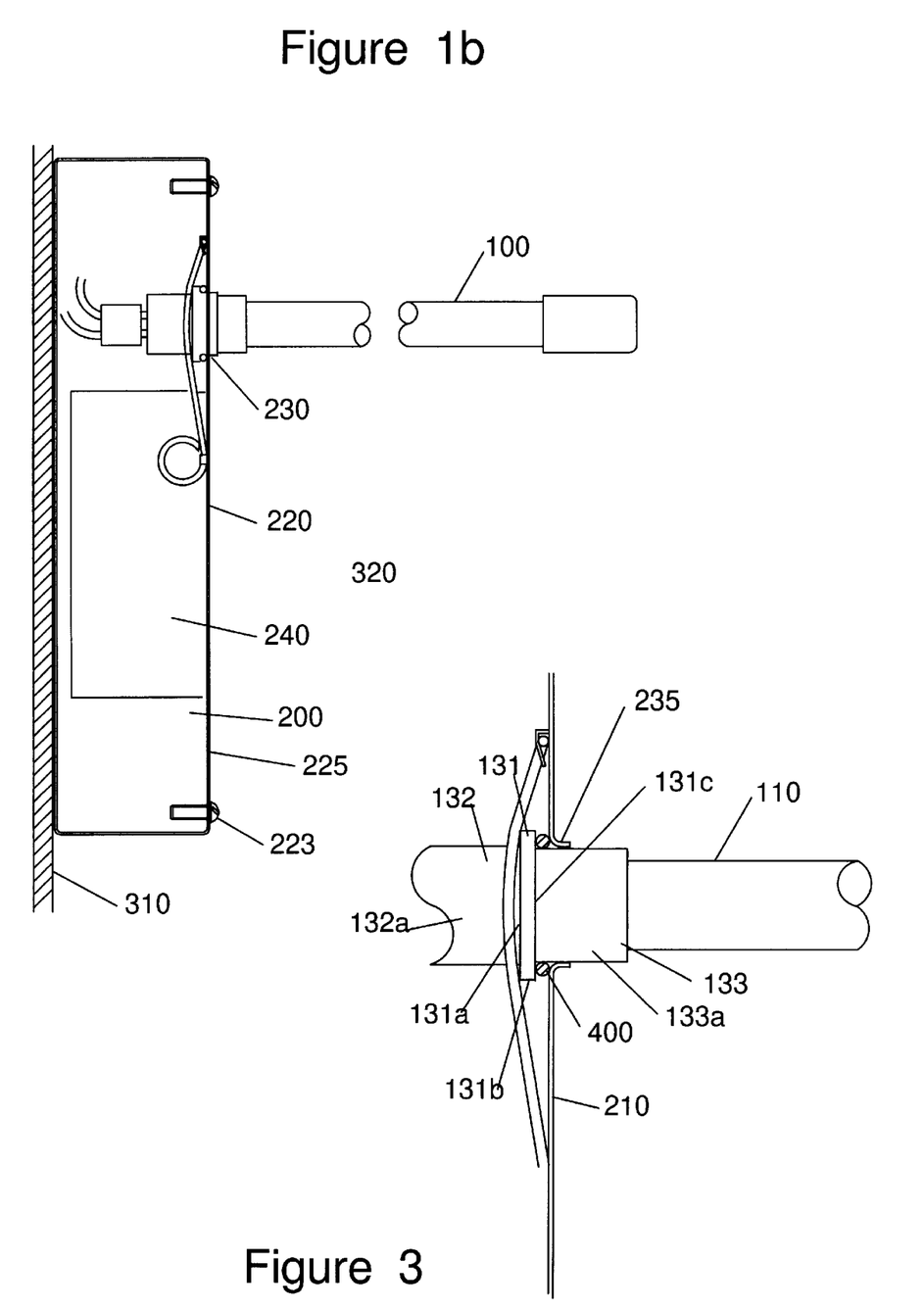
FIG. 1B is a partial side view of a germicidal lamp for internal mounting.
FIG. 3 is a side view of a damping mechanism of the device of FIG. 1A.

FIG. 3 provides a better view of how the stem 135 fits into the through-hole 235.

FIG. 3 shows the ring 131 having a first surface 131a, a second surface 131b and a third surface 131c. As mentioned, the stub 132 has a smaller diameter than the ring 131. The first surface 131a comprises the circular flat surface of the ring 131 which is around the stub 132. The second surface 131b comprises the ring's cylindrical surface. The third surface 131b is opposite the first surface 131a. As mentioned, the hub 133 has a smaller diameter than the ring 131. The third surface 131c comprises the circular flat surface of the ring 131 which is around the hub 133.

The stub 132 has a surface 132a comprising the stub's cylindrical surface.

The hub 133 has a surface 133a comprising the hub's cylindrical surface.

In FIG. 3, a gasket 400 is disposed between the ring 131 and the first wall 210. The gasket 400 is preferably a soft, resilient material such as neoprene which preferably will not break down from UV exposure of exposure to changes in heat and humidity as found in HVAC systems. The gasket 400 preferably has a ring shape. The gasket 400 prevents the ring 131 from touching the first wall 210 and acts as a shock absorber and vibration damper. Thus, pressure applied across the tube 100 is absorbed by the gasket 400 compressing. This prevents damage to the tube 100. The gasket 400 also provides a soft, smooth surface against which the envelope 110 presses during insertion and removal of the tube 100.

Referring now to FIG. 1B, there is shows an alternative embodiment of the invention, a single-tube germicidal lamp for mounting on the inside of an air duct. In this embodiment, the fixture 200 is mounted on the wall 310 inside the air passage 320. The through-hole 230 is on the same wall 220 as the access door 225. Otherwise, this embodiment is substantially the same as the first described embodiment.

Figure 4:
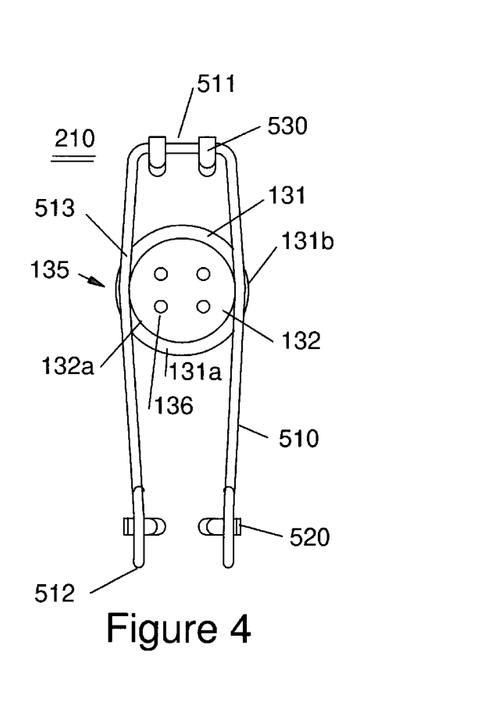
FIG. 4 is a partial rear view of a mounting mechanism of the device of FIG. 1A.

Referring now to FIG. 4, there is shown an embodiment of the mounting mechanism of the invention. The mounting mechanism can be seen to be holding the stem 135 in place. The mounting mechanism is a part of the fixture 200 and is disposed at the through-hole 230. The mounting mechanism preferably comprises a spring clamp. The spring clamp comprises a spring 510, two mounts 530 and two stops 520.

The spring 510 preferably comprises wire, such as spring steel bent in a substantially U shape. The base of the spring's U 511 is fixed by the mounts 530 to the first wall 210 preferably just above the through-hole 230. In FIG. 4, the through hole 230 is concealed by the stem 135. The spring 510 is preferably flat except for ends 512 which are preferably formed into small circles perpendicular to the U 511. The spring 510 includes a central portion 513 having a surface 513a.

The mounts 530 allow the spring 510 to rotate such that the spring 510 can be pivoted about the mounts 530 from a position substantially parallel to the first wall 210 to a position substantially perpendicular to the first wall 210.

The stops 520 hold the spring 510 in compression and parallel to the first wall 210. The stops 520 preferably comprise hooks, with one part of the hook fixed to the first wall 210 and the other part of the hook raised above and somewhat parallel to the first wall 210.

To put the spring 510 in the position shown, the ends 512 are pressed toward one another to reduce the distance between them to less than the distance between the stops 520. Preferably, the ends 512 have a cross-sectional area which allow a person to squeeze them with his fingers. In particular, a person places his thumb against one end 512 and his forefinger against the other end 512 and squeezes the thumb and forefinger together. This causes the ends 512 to be moved together (against the spring's naturally tension) so that the ends 512 are close enough to slip into the stops 520. The ends 512 are therefore pressed against the first wall 210 and slid into the hooks of the stops 520. The stops 520 are positioned such that the spring 510 will be in slight compression when inserted into the stops 520.

Both the mounts 530 and the stops 520 may be formed from the first wall 210 itself. That is, they may be formed by cutting tabs into the first wall 210 and lifting the tabs away from the wall a desired distance. The tabs which comprise the mounts 530 are bent around the spring's U 511 to firmly hold the spring's U 511. The tabs which comprise the stops 520 are raised to allow the ends 512 to slip in and out.

When the tube 100 is in place in the fixture 200 as shown in the figures, the central portion 513 of the spring 510 wraps around the surface 132a of the stub 132 and the surface 513a presses against the stub 132. Preferably, the distance between stops the 520 is less than the diameter of the stub 132. More preferably, the distance between the stops 520 is less than the length of the U 511.

Figure 6:
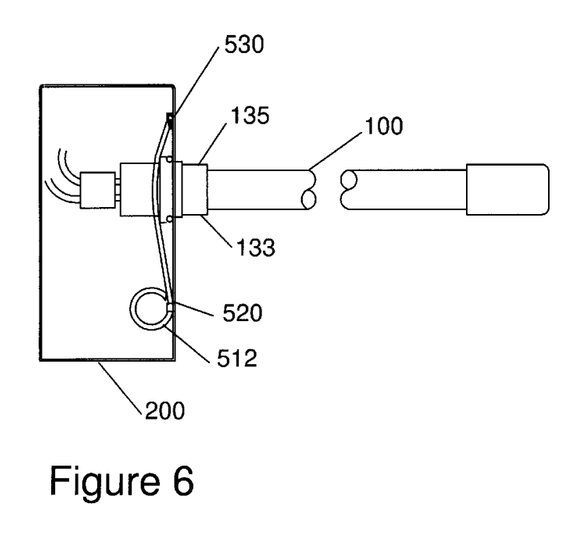
FIG. 6 is a partial side view of the germicidal lamp of FIG. 1A.

The central portion 513 of the spring 510 also lays over the second surface 131b of the ring 131. Because the mounts 530 and stops 520 are mounted on the first wall 210, and the ring 131 has some thickness which puts its surface above the first wall 210, the central portion 513 must also bend around the ring 131. This is better seen from FIG. 6 which shows a cut-away side view of the germicidal lamp. As can be seen, the central portion 513 of the spring 510 becomes somewhat concave as its bends over the first surface 131a of the ring 131. FIG. 6 also shows a socket 600 coupled to the stem 135 to provide electrical connection to the electrodes 136.

The stub 132 and the ring 131 need not be cylindrical as shown. However, the stub 132 must include a surface (such as surface 132a) against which the central portion 513 of the spring 510 can press. The ring 131 must include a surface (such as surface 131a) against which the central portion 513 of the spring 510 can press. Also, the stem 135 must include a surface (such as surface 132c) which will prevent the tube 100 from passing entirely through the through hole 230. Accordingly, the stub 132 and ring 131 may be cross-sectionally square or some other shape, and the stub 132 may include an indentation into which the central portion 513 may fit.

The mounting mechanism of the invention provides a number of benefits. First, it permits fast and simple insertion and removal of the tube 100. Pressure from the spring 510 against the ring 131 holds the tube 100 in place laterally. Pressure from the spring 510 against the stub 132 also holds the tube 100 in place longitudinally. As an added benefit, the tension and compression of the spring clamp with the gaskets absorbs shocks and vibration which might be applied to the tube 100. In particular, it has been found that the gasket, by damping vibration, significantly extends tube life.

Another and more important unexpected benefit is that the tube 100 may be inserted by a technician without the technician touching the envelope 110. Whenever a human touches the envelope 110, oils from the hands are deposited on the envelope 110 and lead to degradation of the envelope and alter and obstruct UV output. If the envelope is touched during installation, it must be cleaned before the tube 100 is energized. Since, in many installations, a technician will be able to access the interior of a duct to clean the envelope 110 with great difficulty, this is quite important. In many installations, the interior of the duct can only be reached by ripping open a wall or cutting open the duct. Since only the stem 135 is touched during installation of the disclosed embodiment, the envelope 110 remains clean.

Installing the tube 100 into the fixture 200 involves the following steps:

1. Open the access door 225 to reveal the interior of the fixture 200.
2. If the spring clamp is closed, open the spring clamp. This is done by squeezing the ends 512 until they clear the stops 520, then pulling the ends 512 away from the first wall 210.
3. Holding the stem 125, insert the free end 120 of the tube 100 through the through-hole 230 until the ring 131 presses against the gasket 400. Alternatively, the gasket may be slid onto the hub 133 until it reaches the ring 131 before the free end 120 is inserted through the through-hole 230.
4. Flip the ends 512 back down toward the first wall 210 so that the central portion 513 slips around the surface 132a of the stub 132.
5. Press the ends 512 together with the thumb and forefinger so surface 513a of the central portion press against the surface 132a and the central portion 513 bends around the stub 132.
6. Continue pressing the ends 512 together until the distance between the ends 512 is less than the distance between the stops 520.
7. Press the ends 512 down against the first wall 210 so that the central portion of the spring 510 presses against the first surface 131a and bends around the ring 131 and the ends 512 slip into the stops 520.
8. Release the ends 512 so that they expand back out and press against the stops 520.
9. Snap the socket 600 onto the stem 135.

Installing the germicidal lamp involves the following steps:

1. Open a small hole 330 in the wall of the air duct having a diameter just slightly larger than the diameter of the hub 133.
2. With the tube 100 already installed in the fixture 200 as described above, insert the free end 100 through the hole 330.
3. Mount the fixture on the outside of the duct wall using screws or other adhesive and electrically connect the fixture to available power.

Alternatively, the fixture may be mounted on the inside of the duct's wall using the germicidal lamp shown in FIG. 1B.

Figure 5:
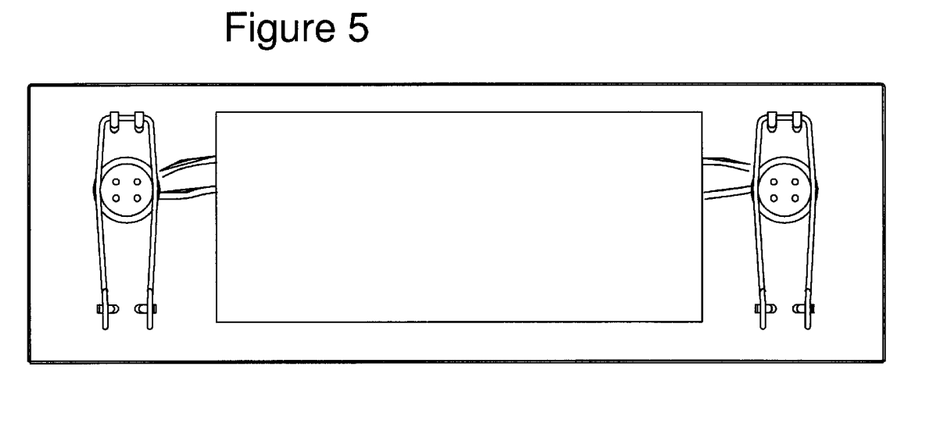
FIG. 5 is a rear view of a double-tube germicidal lamp.
Figure 7:
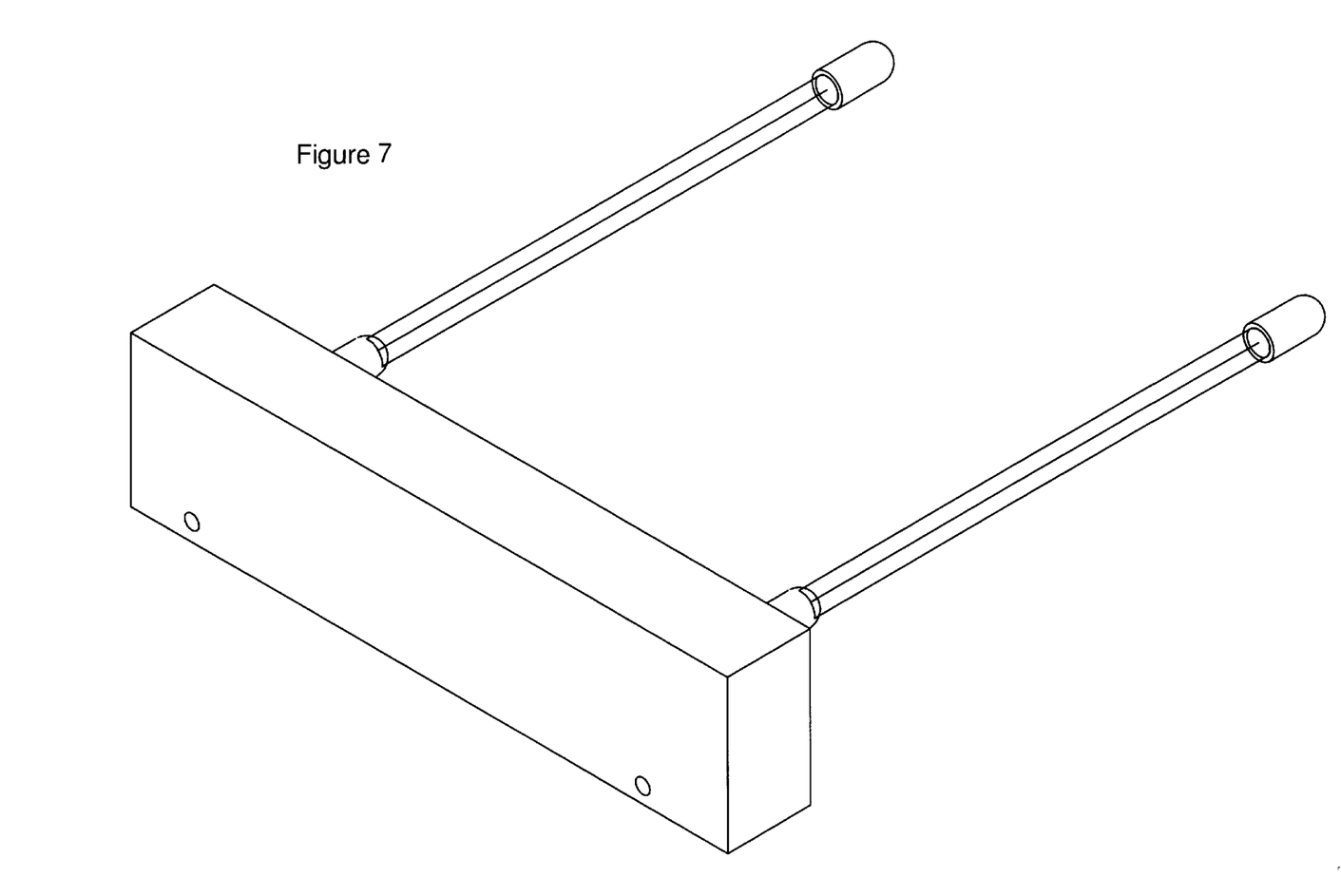
FIG. 7 is an elevated view of the double-tube germicidal lamp of FIG. 5.

FIGS. 5 and 7 show a double-tube embodiment of the invention. Such plural-tube embodiments provide the advantage of additional UV coverage inside the duct while reducing the time needed to install the lamp. These embodiments also result in reduced cost of the fixture, since the plural tubes share a single housing and power supply and shipping is simplified.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

It is claimed:

1. A germicidal lamp for emitting ultraviolet radiation to kill airborne and surface carried microorganisms comprising:
   a single-walled tube having a stemmed end and a free end and comprising
      an envelope disposed between the ends having a first cross-sectional shape,
      a rigid stem secured to the envelope at the stemmed end and comprising a stub and a ring,
      a pliant gasket for absorbing shocks to and vibration of the tube and sealing air flow, the gasket positioned at the stemmed end adjacent the ring on the free end side of the ring, the gasket having a second external cross-sectional shape, and
      plural electrodes mounted in the stem for conducting electricity to the tube, wherein
      the tube is sealed at both ends,
      the envelope and ends define a hollow interior and the tube contains therein a vaporizable material, and
      the electrodes are at least partially exposed to the interior of the tube; and
   a fixture comprising
      a hollow casing having a substantially flat primary wall including a through-hole having a third cross-sectional shape larger than the first cross-sectional shape but smaller than the second cross-sectional shape to thereby permit the envelope to pass but through which the ring will not pass,
      a socket mounted inside of the casing and electrically coupled to the electrodes,
      a spring clamp coupled to the primary wall around the through-hole, the spring clamp comprising a spring, a mount and two stops, the spring comprising wire in a substantially flat U shape, the base of the spring's U being fixed by the mount to the first wall adjacent the through-hole such that the arms of the U are disposed on opposite sides of the through-hole, the mount allowing the spring to rotate such that the spring can be pivoted about the mount from a position substantially parallel to the first wall to a position substantially perpendicular to the first wall, the stops holding the spring in compression and parallel to the first wall;
      wherein the spring clamp wraps at least partially around the stem and presses the ring against the gasket and the gasket presses against the primary wall and thereby holds the gasket and tube in place and the tube in the fixture;
      whereby the spring clamp and the gasket absorb shocks to and vibration of the tube.

2. A germicidal lamp set forth in claim 1, the primary wall further including a depression around the through-hole from the substantial flatness of the primary wall adapted to receive the gasket, wherein the primary wall comprises an inner surface and an outer surface, the spring clamp is mounted on the inner surface, and the depression extends from the inner surface toward the outer surface.

3. A germicidal lamp as set forth in claim 1, the casing comprising a six-sided box with an access door to the inside of the box disposed opposite the through-hole, the casing further including means for attaching the casing to an air duct or other surface, whereby the tube may be removed by opening the access door, disconnecting the socket from the electrodes, releasing the spring clamp and pulling the tube through the through-hole.

4. A germicidal lamp for emitting ultraviolet radiation to kill airborne and surface carried microorganisms comprising:
   a sealed single-walled tube defining an interior and comprising an elongate hollow envelope fixed to a stem and plural electrodes for providing electric current to the tube, the electrodes fixed to the stem and at least partially exposed outside of the stem and at least partially exposed to the interior of the tube, the envelope having a maximum first cross section, the stem having a maximum second cross section, wherein the first cross-section is smaller than the second cross-section;
   a fixture having an inside and an outside, the fixture comprising:
      a hollow casing having a primary wall with a through-hole, the casing substantially defining the inside of the fixture,
      a power supply fixed inside of the casing,
      plural electrical contacts coupled to the power supply, disposed in the casing opposite the through-hole, and adapted to contact the electrodes when the tube is installed in the fixture,
      a spring clamp fixed to the wall and disposed at the through-hole for securing the stem to the wall such that the weight of the tube is supported; and
   a flexible, resilient gasket disposed between the through-hole and the stem;
   wherein the spring clamp presses the stem against the gasket and the gasket presses against the primary wall and thereby holds the gasket in place and the tube in the fixture;
   whereby the spring clamp and the gasket absorb shocks to and vibration of the tube.

5. A germicidal lamp as set forth in claim 4 wherein the gasket is fixed to the stem.

6. A germicidal lamp as set forth in claim 4 wherein the gasket is fixed to the wall.

7. A germicidal lamp as set forth in claim 4, the casing comprising a six-sided box with an access door to the inside of the box, the casing further including means for attaching the casing to a surface, whereby the tube may be removed by opening the access door, disconnecting the electrodes from the contacts, releasing the spring clamp and pulling the tube through the through-hole.

8. A germicidal lamp as set forth in claim 7 for mounting on a surface with the tube facing away from the surface, wherein the access door is located on the primary wall.

9. A germicidal lamp as set forth in claim 7 for mounting on a surface with the tube passing through a hole in the surface, wherein the access door is disposed opposite the wall.

10. A method of installing a single-walled germicidal lamp tube into a germicidal lamp fixture, the tube having a stemmed end and a free end and comprising an envelope disposed between the ends, a stem secured to the envelope at the stemmed end and comprising a stub and a ring, the ring situated closer to the free end than the stub, the fixture comprising a hollow casing having a substantially flat primary wall including a through-hole through which the envelope may pass but through which the ring will not pass and a spring clamp coupled to the primary wall around the through-hole, the spring clamp comprising a U-shaped member having two arms each with an end, a mount for pivotally holding a central portion of the U-shaped member to the primary wall and two stops for removably holding the ends of the arms to the primary wall, the method comprising the steps of:

(a) holding the stem, inserting the free end of the tube through the through-hole until the ring presses against a pliable gasket and the gasket presses against the primary wall;

(b) flipping the ends of the spring toward the primary wall so that the arms of the spring slip around the surface of the stub;

(c) pressing the ends of the spring together so that the arms press against the surface of the ring and stub and bend around the stub;

(d) continuing to press the ends of the spring together until the distance between the ends is less than the distance between the stops;

(e) pressing the ends down against the primary wall so that the arms of the spring press against the first surface of the ring and bend around the ring and the ends slip into the stop, and the ring presses firmly against the gasket and the gasket presses firmly against the primary wall;

(f) releasing the ends so that they expand back out and press against the stops under compression and the spring clamp holds the tube in the fixture;

whereby the spring clamp and the casket absorb shocks to and vibration of the tube.

11. A method of installing a germicidal lamp tube into a germicidal lamp fixture as set forth in claim 10 wherein the fixture includes an access door opposite the through-hole, the method further comprising the step of opening the access door to reveal the interior of the fixture.

12. A method of installing a germicidal lamp tube into a germicidal lamp fixture as set forth in claim 10 wherein the fixture comprises a socket, the method further comprising the step of pressing the socket onto the stem.

13. A method of installing a germicidal lamp tube into a germicidal lamp fixture as set forth in claim 10 wherein the gasket is slid onto the tube from the free end until the gasket reaches the ring before the free end is inserted through the through-hole.

14. A method of installing a germicidal lamp in an air duct, the air duct having a wall with an inside surface and an outside surface, the germicidal lamp comprising a fixture and a single-walled, single-ended tube comprising an envelope and an end, the envelope having a first cross-section, the end having a second-cross section larger than the first cross-section of the envelope, the fixture defining a first hole having a third cross-section larger than the first cross-section of the envelope, the tube having a stemmed end and a free end and comprising an envelope disposed between the ends, a stem secured to the envelope at the stemmed end and comprising a stub and a ring, the ring situated closer to the free end than the stub, the fixture comprising a hollow casing having a substantially flat primary wall including a through-hole through which the envelope may pass but through which the ring will not pass and a spring clamp coupled to the primary wall around the through-hole, the spring clamp comprising a U-shaped member having two arms each with an end, a mount for pivotally holding a central portion of the spring clamp to the primary wall and two stops for removably holding the ends of the arms to the primary wall, the method comprising the steps of:

opening a second hold in the wall of the air duct having a fourth cross-section larger than the first cross-section of the envelope, wherein at least one of the third cross-section and the fourth cross-section is smaller than the second cross-section to prevent the stem and ring from passing through both the first hole in the fixture and the second hole in the wall of the air duct;

mounting the fixture on the outside surface of the duct wall so that the first hole is disposed over the second hole;

electrically connecting the fixture to available power;

inserting the free end of the tube through the first hole and the second hole;

fixing the tube to the fixture by the steps of:
holding the stem, inserting the free end of the tube through the through-hole;

flipping the ends of the spring toward the primary wall so that the arms of the spring slip around the surface of the stub;

pressing the ends of the spring together so that the arms press against the surface of the stub and bend around the stub;

continuing to press the ends of the spring together until the distance between the ends is less than the distance between the stops;

pressing the ends down against the primary wall so that the arms of the spring press against the first surface of the ring and bend around the ring and the ends slip into the stops; and releasing the ends so that they expand back out and press against the stops under compression; and electrically connecting the tube to the fixture.

15. The method of installing a germicidal lamp in an air duct as set forth in claim 14 wherein the envelope has a circular cross-section, and the first hole and the second hole are circular, and the first cross-section, third cross-section and fourth cross-section are circular and are defined by respective diameters.

* * * * *

UNITED STATES PATENT AND TRADEMARK OFFICE
CERTIFICATE OF CORRECTION

PATENT NO. : 5,866,076

DATED : Feb. 2, 1999

INVENTOR(S) : Forrest B. Fencl, Robert M. Culbert

It is certified that error appears in the above-indentified patent and that said Letters Patent is hereby corrected as shown below:

In claim 10, col. 11, line 24, please delete the word "casket" and substitute in place thereof --gasket--;

Signed and Sealed this

Sixteenth Day of November, 1999

Attest:

Q. TODD DICKINSON

*Attesting Officer*    *Acting Commissioner of Patents and Trademarks*